United States Patent [19]

Buchecker et al.

[11] Patent Number: 5,518,653

[45] Date of Patent: May 21, 1996

[54] OPTICALLY ACTIVE METHYL DIOXANES

[75] Inventors: Richard Buchecker, Zurich; Jürg Fünfschilling, Basel; Martin Schadt, Seltisberg, all of Switzerland

[73] Assignee: Hoffmann-La Roche Inc., Nutley, N.J.

[21] Appl. No.: 371,617

[22] Filed: Jan. 12, 1995

Related U.S. Application Data

[63] Continuation of Ser. No. 908,618, Jun. 29, 1992, abandoned, which is a continuation of Ser. No. 692,759, Apr. 29, 1991, abandoned.

[30] Foreign Application Priority Data

May 15, 1990 [CH] Switzerland ............................ 1635/90

[51] Int. Cl.$^6$ .......................... C09K 19/34; C07D 319/06
[52] U.S. Cl. ........................................ 252/299.61; 549/369
[58] Field of Search ........................ 252/299.61; 549/369

[56] References Cited

U.S. PATENT DOCUMENTS

| | | | |
|---|---|---|---|
| 4,264,148 | 4/1981 | Gobl-Wunsch et al. | 350/346 |
| 4,676,604 | 6/1987 | Petrzilka | 350/350 R |
| 4,704,227 | 11/1987 | Krause et al. | 252/299.61 |
| 4,726,911 | 2/1988 | Krause et al. | 252/299.61 |
| 4,755,323 | 7/1988 | Eidenschink et al. | 252/299.61 |
| 4,770,503 | 9/1988 | Buchecker et al. | 350/350 R |
| 5,013,476 | 5/1991 | Boller et al. | 252/299.61 |

FOREIGN PATENT DOCUMENTS

| | | |
|---|---|---|
| 257049 | 1/1987 | European Pat. Off. |
| 3437935 | 10/1984 | Germany |

OTHER PUBLICATIONS

Derwent Abstract of EP 257,049 No. 87–250188/35.
Derwent Abstract of DE 3,437,935 No. 86–113699118.

*Primary Examiner*—Gary L. Geist
*Assistant Examiner*—C. Harris
*Attorney, Agent, or Firm*—George M. Gould; George W. Johnston

[57] ABSTRACT

Optically active compounds of the formula

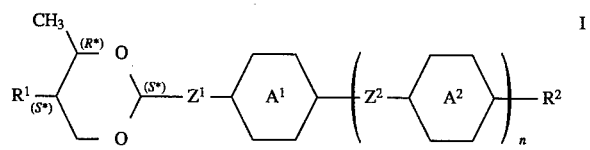

wherein n stands for the number 0 or 1; $Z^1$ is a single covalent bond or —$CH_2CH_2$—; $Z^2$ is a single covalent bond, —$CH_2CH_2$—, —$CH_2O$—, —$OCH_2$—, —COO— or —OOC—; rings $A^1$ and $A^2$ each independently represent trans-1,4-cyclohexylene or optionally halogen-, cyano- and/or methyl-substituted 1,4-phenylene in which optionally 1 CH group or 2 CH groups is/are replaced by nitrogen; $R^2$ is a group $R^4$ or a group of the formula

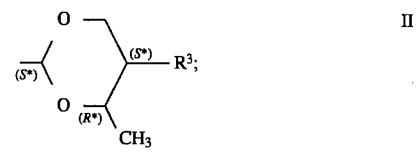

$R^4$ is cyano, halogen, —$OCY^1F_2$, —$CY^1F_2$ or an alkyl group in which optionally one >CH—CH< is replaced by >C=C< and/or optionally one methylene group or two non-adjacent methylene groups is/are replaced by —O—, —COO— and/or —OOC— and/or optionally one methylene group is replaced by —$CHY^2$—; $Y^1$ is hydrogen or fluorine; $Y^2$ is halogen, cyano or methyl; $R^1$ and $R^3$ denote alkyl in which optionally one >CH—CH< is replaced by >C=C< and/or optionally one methylene group or two non-adjacent methylene groups is/are replaced by —O— and/or optionally one or more hydrogen atoms is/are replaced by fluorine; and (S*) and (R*) denote the relative configurations of the chiral carbon atoms, as well as liquid crystalline mixtures which contain such compounds and their use for optical and electro-optic purposes.

14 Claims, No Drawings

OPTICALLY ACTIVE METHYL DIOXANES

This is a continuation of U.S. application Ser. No. 07/908,618, filed Jun. 29, 1992, which is a continuation of U.S. application Ser. No. 07/692,759, filed Apr. 29, 1991 (now abandoned).

BACKGROUND

1. Field of the Invention

The present invention is concerned with novel chiral dopants for liquid crystals as well as liquid crystalline mixtures which contain such dopants and their use for optical and electro-optical purposes.

2. General Discussion

Liquid crystal materials for electro-optical indicating devices frequently contain one or more optically active additives for the induction of a chiral structure. For example, for use in indicating devices having a twisted nematic structure a nematic liquid crystal is doped with an optically active additive, for example in order to prevent a reversal of the twisting direction (reverse twist) in TN cells (twisted-nematic) or in order to achieve a sufficient twisting in cells having a highly twisted nematic structure such as STN cells (super twisted-nematic), SBE cells (super birefringence effect) or OMI cells (optical mode interference). Further, cholesteric liquid crystals for phase-change cells can preferably consist of a nematic basic material and one or more optically active dopants and ferroelectric liquid crystals for indicating devices based on chiral tilted smectic phases can preferably consist of a material having a twisted smectic phase and one or more active dopants.

The electro-optical characteristics of liquid crystal indicating devices are temperature-dependent, which is especially troublesome in the case of multiplex operation. It is, however, known that this temperature dependence can be compensated for at least partially by the addition of chiral dopants which induce a decreasing pitch with increasing temperature. Such an inverse temperature dependence has been found only for a few compounds. It can, however, also be achieved by using at least two chiral dopants which have a different relative temperature dependence and which induce a different twisting direction (U.S. Pat. No. 4,264,148). Of course, this requires for the most part a relatively high amount of chiral dopants.

Cholesteric liquid crystals reflect light in a wavelength range for which the wavelength is approximately equal to the helical pitch. The spectral width of this reflected light can be varied by a suitable choice of the liquid crystal. The reflected light is completely circularly polarized. The direction of rotation of the reflected light depends on the direction of rotation of the cholesteric helical structure. The light circularly polarized in the opposite direction is transmitted without adsorption. These properties can be utilized for the production of optical filters, polarizers, analyzers etc. Further, cholesteric liquid crystals have also variously been used for thermochromic applications and in cosmetic preparations.

Cholesteric liquid crystals for the above applications can o preferably consist of a nematic or cholesteric basic material and one or more chiral dopants, which permits a simple adjustment of the desired helical pitch.

In order to produce cholesteric mixtures having a pitch in the range of the wavelength of visible light, the chiral dopants should have a twisting capacity which is a high as possible and should have a good solubility in usual liquid crystal materials. Furthermore, the chiral dopants should have an adequate stability, should have a good compatibility with the mesophase type of the liquid crystal material and should not restrict the mesophase range too stongly. Such properties would also be desirable for chiral dopants for producing the twisted nematic structures referred to earlier, since their amount can be held low in order that the properties of the liquid crystal material are influenced only immaterially. The use of chiral dopants in ferroelectric liquid crystals serves primarily to produce to change a twisting of the tilted smectic phase and to induce a spontaneous polarization. The chiral dopants should have an adequate stability, should have a good compatibility with the tilted smectic liquid crystal and should not restrict the mesophase range too strongly. Further, it would be desirable for the twisting and the spontaneous polarization to be adjusted independently of each other as far as possible and for the viscosity of the chiral dopants to be comparatively low.

SUMMARY OF THE INVENTION

The invention is concerned with optically active 4-methyl-1,3-dioxane derivatives of the formula

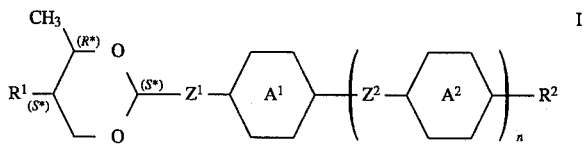

wherein n stands for the number 0 or 1; $Z^1$ denotes a single covalent bond or —$CH_2CH_2$—; $Z^2$ denotes a single covalent bond, —$CH_2CH_2$—, —$CH_2O$—, —$OCH_2$—, —COO— or —OOC—; rings $A^1$ and $A^2$ each independently represent trans-1,4-cyclohexylene or optionally halogen-, cyano- and/or methyl-substituted 1,4-phenylene in which optionally 1 CH group or 2 CH groups is/are replaced by nitrogen; $R^2$ denotes a group $R^4$ or a group of the formula

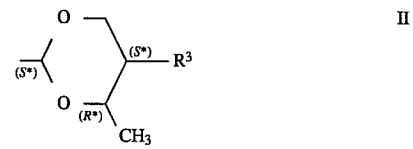

$R^4$ signifies cyano, halogen, —$OCY^1F_2$, —$CY^1F_2$ or an alkyl group in which optionally one >CH—CH< is replaced by >C=C< and/or optionally one methylene group or two non-adjacent methylene groups is/are replaced by —O—, —COO— and/or —OOC— and/or optionally one methylene group is replaced by —$CHY^2$—; $Y^1$ denotes hydrogen or fluorine; $Y^2$ signifies halogen, cyano or methyl; $R^1$ and $R^3$ denote alkyl in which optionally one >CH—CH< is replaced by >C=C< and/or optionally one methylene group or two non-adjacent methylene groups is/are replaced by —O— and/or optionally one or more hydrogen atoms is/are replaced by fluorine; and (S*) and (R*) denote the relative configurations of the chiral carbon atoms.

The compounds in accordance with the invention are colourless, have a good solubility in usual liquid crystals and have an especially good compatibility with nematic, cholesteric and tilted smectic phases. They have an adequate stability towards electric and magnetic fields and frequently themselves have liquid crystalline properties. Although the chiral dioxane ring is relatively non-polar, in tilted smectic phases they induce a comparatively high spontaneous polarization. Further, they have a high twisting capacity and a comparatively low viscosity. If desired, the twisting capacity and spontaneous polarization can be intensified or modified by chiral end groups. Further, by lateral substitution, inter alia, the spontaneous polarization can be altered relative to the twisting capacity; for example, by lateral substitution (for example with halogen) on a benzene ring $A^1$ in the orthoposition to the dioxane ring the sign of the spontaneous polarization can be reversed with the same helicity. This permits a variation of the twisting and of the spontaneous polarization which are to a large extent different from each other.

DETAILED DESCRIPTION OF THE INVENTION

The invention is directed to optically active compounds of the formula

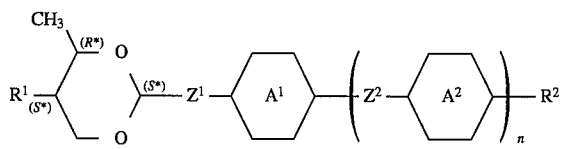

wherein n is the integer 0 or 1; $Z^1$ is a single covalent bond or —CH$_2$CH$_2$—; $Z^2$ is a single covalent bond, —CH$_2$CH$_2$—, —CH$_2$O—, —OCH$_2$—, —COO— or —OOC—; rings $A^1$ and $A^2$ each independently are trans-1,4-cyclohexylene, or optionally halogen-, cyano and/or methyl-substituted 1,4-phenylene, pyridine-2,5-diyl, pyrimidine-2,5-diyl, pyrazine or pyridazine; $R^2$ is a group $R^4$ or a group of the formula

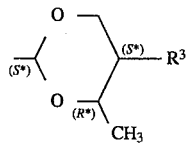

$R^4$ is cyano, halogen, —OCY$^1$F$_2$, —CY$^1$F$_2$ or alkyl, alkenyl, alkoxy, alkenyloxy, alkoxyalkyl, alkenyloxyalkyl, alkoxycarbonyl, alkoxycarbonylalkoxy, alkoxycarbonylalkoxycarbonyl or alkanoyloxy, any of which may be unsubstituted or substituted with at least one of halogen, cyano or methyl; $Y^1$ is hydrogen or fluorine; $R^1$ and $R^3$ each are alkyl, alkoxy, alkenyl, alkenyloxy, alkoxyalkyl or alkenyloxyalkyl, which are unsubstituted or substituted with at least one fluorine; and (S*) and (R*) denote the relative configurations of the chiral carbon atoms, and optical antipodes thereof.

The compounds in accordance with the invention are colourless, have a good solubility in usual liquid crystals and have an especially good compatibility with nematic, cholesteric and tilted smectic phases. They have an adequate stability towards electric and magnetic fields and frequently themselves have liquid crystalline properties. Although the chiral dioxane ring is relatively non-polar, in tilted smectic phases they induce a comparatively high spontaneous polarization. Further, they have a high twisting capacity and a comparatively low viscosity. Of desired, the twisting capacity and spontaneous polarization can be intensified or modified by chiral end groups. Further, by lateral substitution, inter alia, the spontaneous polarization can be altered relative to the twisting capacity; for example, by lateral substitution (for example with halogen) on a benzene ring $A^1$ in the orthoposition to the dioxane ring the sign of the spontaneous polarization can be reversed with the same helicity. This permits a variation of the twisting and of the spontaneous polarization which are to a large extent different from each other.

The term "halogen" denotes in the scope of the present invention fluorine, chlorine, bromine and iodine, especially fluorine, chlorine and bromine.

The term "optionally halogen-, cyano- and/or methyl-substituted 1,4-phenylene in which optionally 1 CH group or 2CH groups is/are replaced by nitrogen" embraces groups such as 1,4-phenylene, 2-fluoro-1,4-phenylene, 2-chloro-1,4-phenylene, 2-bromo- 1,4-phenylene, 2-cyano-1,4-phenylene, 2 -methyl-1,4-phenylene, 2,3-difluoro-1,4-phenylene, 2,3 -dicyano-1,4-phenylene, pyridine-2,5-diyl, pyrimidine-2,5-diyl, pyrazine-2,5-diyl, pyridazine-3,6-diyl and the like.

The term "alkyl group in which optionally one >CH—CH< is replaced by >C=C< and/or optionally one methylene group or two non-adjacent methylene groups is/are replaced by —O—, —COO— and/or —OOC— and/or optionally one methylene group is replaced by —CHY$^2$—" embraces straight-chain and branched (optionally chiral) residues such as alkyl, 1E-alkenyl, 3E-alkenyl, 4-alkenyl, alkenyl having a terminal double bond, alkoxy, 2E-alkenyloxy, 3-alkenyloxy, alkenyloxy having a terminal double bond, alkoxyalkyl, alkenyloxyalkyl, alkoxycarbonyl, alkoxycarbonylalkoxy, alkoxycarbonylalkoxycarbonyl, alkanoyloxy, 1-haloalkyl, 2-haloalkyl, 2-haloalkoxy, 2-haloalkanoyloxy, 1-cyanoalkyl, 2-cyanoalkyl, 2-cyanoalkoxy, 1-methylalkyl, 2-methylalkyl, 1-methylalkoxy, 2-methylalkoxy and the like. Examples of preferred residues are methyl, ethyl, propyl, butyl, pentyl, hexyl, heptyl, octyl, nonyl, decyl, undecyl, dodecyl, 1-methylpropyl, 1-methylheptyl, 2-methylbutyl, vinyl, 1E-propenyl, 1E-butenyl, 1E-pentenyl, 3-butenyl, 3E-pentenyl, 3E-hexenyl, 3E-heptenyl, 4-pentenyl, 4Z-hexenyl, 5-hexenyl, 6-heptenyl, 7-octenyl, methoxy, ethoxy, propyloxy, butyloxy, pentyloxy, hexyloxy, heptyloxy, octyloxy, nonyloxy, decyloxy, undecyloxy, dodecyloxy, 1-methylpropyloxy, 1-methyl heptyloxy, 2-methylbutyloxy, 3-methylpentyloxy, allyloxy, 2E-butenyloxy, 2E-pentenyloxy, 2E-hexenyloxy, 3-butenyloxy, 3Z-pentenyloxy, 4-pentenyloxy, 5-hexenyloxy, 6-heptenyloxy, 7-octenyloxy, methoxymethyl, ethoxymethyl, propyloxymethyl, allyloxy- methyl, methoxycarbonyl, ethoxycarbonyl, propyloxycarbonyl, 1-methylpropyl-oxycarbonyl (=2-butyloxycarbonyl), 1-methylpentyloxycarbonyl (=2-hexyloxycarbonyl), 1-methylheptyloxycarbonyl (=2-octyloxycarbonyl), 1-(methoxycarbonyl)ethoxy, 1-(ethoxy carbonyl)ethoxy, 1-(methoxycarbonyl)ethoxycarbonyl, 1 -(isobutyloxy-carbonyl)ethoxycarbonyl, acetoxy, propionyloxy, butyryloxy, 2-fluorohexanoyloxy, 2-fluoropentyloxycarbonyl, 2-fluoro-3-methylbutyloxycarbonyl, 2-fluoro-4-methyl pentyloxy-carbonyl and the like.

The term "alkyl in which optionally one >CH—CH< is replaced by >C=C< and/or optionally one methylene group or two non-adjacent methylene groups is/are replaced by —O— and/or optionally one or more hydrogen atoms is/are replaced by fluorine" embraces alkyl, alkenyl (for example 3E-alkenyl, 4-alkenyl, alkenyl having a terminal double bond), alkoxyalkyl (for example 2-alkoxyethyl, 3-alkoxypropyl), fluoroalkyl and the like. The residues can be straight-chain or branched (optionally chiral). Examples of preferred residues are methyl, ethyl, propyl, butyl, pentyl, hexyl, heptyl, octyl, nonyl, decyl, undecyl, dodecyl, 1-methylpropyl, 1-methylheptyl, 2-methylbutyl, 3-butenyl, 3E-pentenyl, 3E-hexenyl, 3E-heptenyl, 4-pentenyl, 4Z-hexenyl, 5-hexenyl, 6-heptenyl, 7-octenyl, 2-methoxyethyl, 3-methoxypropyl, 1-fluoropropyl, 2-fluoropentyl and the like.

The relative configurations of the chiral carbon atoms denoted by (S*) and (R*) in formula I and the following formulas are that the denoted carbon atoms as indicated have the (S)- or (R)-configuration or that all denoted carbon atoms have the mirror image configuration. The formulas therefore embrace in each case the diastereoisomer in which (S*) stands for the (S)-configuration and (R*) stands for the (R)-configuration as well as their optical antipodes in which (S*) stands for the (R)-configuration and (R*) stands for the (S)-configuration.

Ring $A^2$ in formula I above can preferably are 1,4-phenylene or halogen-substituted 1,4-phenylene. 2-Fluoro-1,4-phenylene and 2,3-difluoro-1,4-phenylene are preferred halogen-substituted rings.

$Z^2$ can preferably denote a single covalent bond, —CH$_2$CH$_2$— or —OOC—, especially a single covalent bond. $Z^1$ can preferably denote a single covalent bond.

Accordingly, there are especially preferred in general those compounds of formula I in which ring $A^2$ represents 1,4-phenylene, 2-fluoro-1,4-phenylene or 2,3-difluoro-1,4-phenylene and $Z^1$ and $Z^2$ denote single covalent bonds. Ring $A^1$ can preferably represent pyridine-2,5-diyl, pyrimidine-2,5-diyl, trans-1,4-cyclohexylene or optionally halogen-, cyano- and/or methyl-substituted 1,4-phenylene. Especially preferred significances of ring $A^1$ are trans-1,4-cyclohexylene, 1,4-phenylene and halogen-substituted 1,4-phenylene, especially 1,4-phenylene, 2-fluoro-1,4-phenylene, 2,3-difluoro- 1,4-phenylene and 2-chloro 1,4-phenylene.

Preferred sub-groups of compounds of formula I are the compounds of the formulas

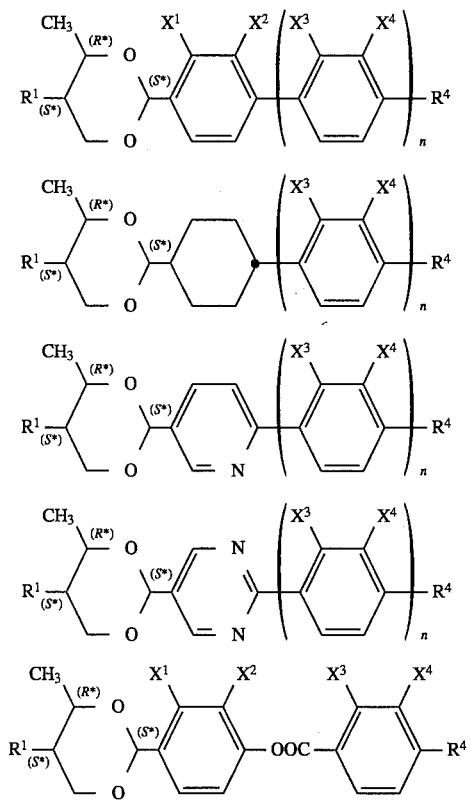

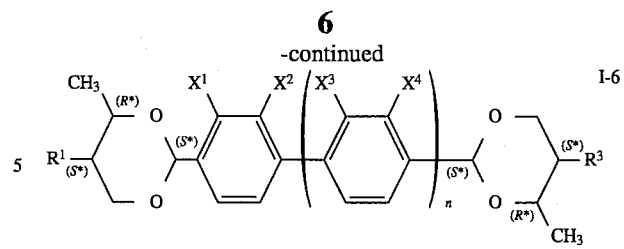

wherein $R^4$ is cyano, halogen, —OCY$^1$F$_2$, —CY$^1$F$_2$ or alkyl, alkenyl, alkoxy, alkenyloxy, alkoxyalkyl, alkenyloxyalkyl, alkoxycarbonyl, alkoxycarbonylalkoxy, alkoxycarbonyl-alkoxycarbonylalkoxy or alkanoyloxy any of which may be unsubstituted or substituted with at least one of halogen, cyan or methyl; $Y^1$, $X^1$, $X^2$, $X^3$ and $X^4$ each independently denote hydrogen or halogen; and n, $R^1$, $R^3$, (S*) and (R*) have the above significances.

The residues $R^1$, $R^3$ and $R^4$ in formulas I and I-1 to I-6 above can each independently preferably have 1 to about 18 carbon atoms. Residues with 1 to 12 carbon atoms are in general especially preferred.

The residues $R^1$ and $R^3$ preferably are alkyl, especially straight-chain alkyl. If desired, however, the residues $R^1$ and $R^3$ can have a double bond, 1–2 oxygen atoms, one or more fluorine atoms and/or chain-branchings, for example when a slight modification of the properties is desired or when chiral residues are desired. $R^1$ and $R^3$ can especially also are identical residues.

Preferred residues $R^4$ in formulas I and I-1 to I-5 above are cyano, fluorine, chlorine, difluoromethoxy, trifluoromethoxy, difluoromethyl, trifluoromethyl, alkyl, alkoxy, alkoxycarbonyl, 1-(alkoxycarbonyl)ethoxycarbonyl, alkanoyloxy, 2-fluoroalkanoyloxy, alkenyl and alkenyloxy.

Preferred residues $R^2$ are the residues referred to at being preferred for $R^4$ as well as the groups of formula II in which $R^3$ has the significances referred to above as being preferred.

The substituents $X^1$, $X^2$, $X^3$ and $R^4$ in formulas I-1 to I-6 above can each individually preferably are hydrogen, fluorine or chlorine. In each case a maximum of one or two of the substituents is preferably different from hydrogen. There are especially preferred in general those compounds of formulas I-1 to I-6 in which $X^1$ denotes hydrogen, fluorine or chlorine, $X^2$ and X3 denote hydrogen and $X^4$ denotes hydrogen, fluorine or chlorine.

The compounds of formula I can be prepared by reacting a diol of the formula

with an aldehyde of the formula

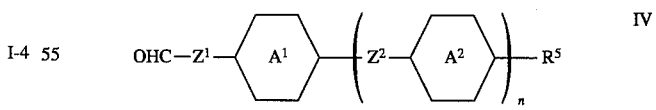

wherein $R^5$ denotes a group $R^2$ or formyl and $R^1$, $R^2$, $Z^1$, $Z^2$, n, (R*), (S*) and the rings $A^1$ and $A^2$ have the above significances, or an acetal thereof.

The reaction of the aldehyde of formula IV or of a suitable acetal (for example the dimethyl acetal) with the diol of formula III can be effected in a manner known per se. Preferably, the reaction is effected in an inert organic solvent (for example, an aromatic hydrocarbon such as benzene, toluene or xylene) in the presence of a catalytic amount of an organic or inorganic acid such as p-toluenesulfonic acid, sulfuric acid or dry hydrogen chloride. The temperature and pressure are not critical. However, the reaction is preferably carried out at atmospheric pressure and at the reflux temperature while separating the water which is formed.

When $R^2$ in formula I is a group of formula II, the formation of the two dioxane rings can be effected as indicated above successively or—especially when $R^1$ and $R^3$ are identical—also simultaneously.

When $Z^2$ and/or $R^2$ have ester groups, the esterification is preferably effected only after the formation of the dioxane ring. Further, when $R^1$, $Z^2$ and/or $R^2$ have ether groups, the etherification can, if desired, also be effected after the formation of the dioxane ring.

The aldehydes of formula IV are known or are analogues of known compounds and can be prepared according to known methods.

The preparation of the diols of formula III can be effected in a manner known per se. A preferred method comprises introducing the substituent $R^1$ in the 2-position of an alkyl 3-hydroxybutyrate— for example by reaction with the corresponding alkyl halide, alkenyl halide etc. in the presence of a suitable base in an analogous manner to Tetrahedron 40, 1269 (1984)—and subsequently reducing the ester group. For example, ethyl 3ohydroxybutyrate can be reacted with an alkyl bromide, alkenyl bromide and the like in the presence of a base such as lithium diisopropylamide and the ethyl 3-hydroxy-2$R^1$-butyrate obtained can be reduced with lithium aluminium hydride.

The compounds in accordance with the invention are suitable as chiral dopants for liquid crystalline mixtures. The invention is therefore also concerned with a liquid crystalline mixture having at least two components, wherein at least one component is an optically active compound of formula I.

Preferably, the mixtures in accordance with the invention contain a liquid crystalline carrier material and one or more optically active compounds of formula I. Suitable carrier materials are basically all liquid crystal materials which have a twistable liquid crystal phase with an adequate mesophase range. The liquid crystalline carrier material can be a single compound or a mixture and preferably has a clearing point of at least about 60° C. The compounds of formula I are especially suitable as chiral dopants for carrier materials having a nematic, cholesteric or tilted smectic (preferably smectic C) phase.

The amount of chiral dopants of formula I is determined to a large extent by the twisting capacity, the spontaneous polarization and the desired pitch. The amount of chiral dopant can therefore vary in a wide range depending on the application and can, for example, amount to about 0.1–40 wt. %. For indicating devices based on liquid crystals having a twisted nematic structure there is for the most part required, depending on the type of cell and cell thickness, a pitch of about 3–40 mm and therefore a correspondingly smaller amount, for example about 0.1–3 wt. %, is sufficient. On the other hand, for applications which are based on the reflection of visible light by cholesteric layers, pitches of less than 2 mm, for example about 0.4–0.6 mm, are required, which requires a correspondingly higher amount of chiral dopant. For such o applications and in the case of use in tilted smectic phases an amount of about 3–30 wt. %, especially about 5–20 wt. %, of optically active dopants of formula I is in general preferred.

The mixtures in accordance with the invention which have a cholesteric phase can preferably contain, in addition to one or more optically active compounds of formula I, one or more compounds of the following formulas as components of the nematic or cholesteric carrier material:

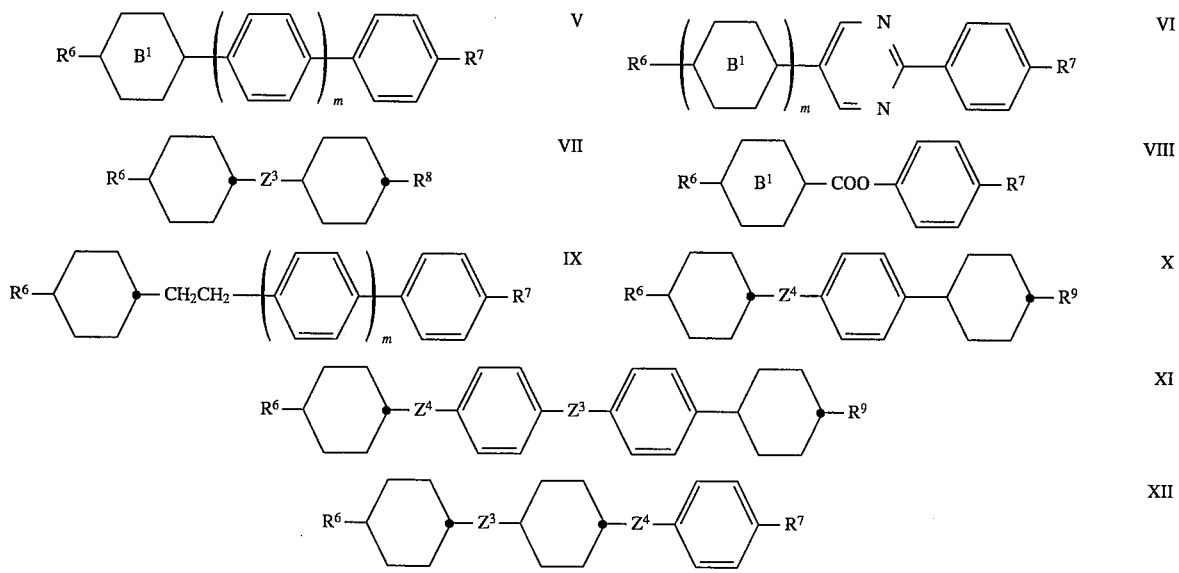

wherein m stands for the number 0 or 1; ring $B^1$ represents 1,4-phenylene or trans-1,4-cyclohexylene; $R^6$ denotes alkyl, alkenyl or on a benzene ring also alkoxy or alkenyloxy; $R^7$ is cyano, alkyl, alkoxy, alkenyl or alkenyloxy; $Z^3$ denotes a single covalent bond or —$CH_2CH_2$—; $R^8$ is cyano, alkyl, alkoxy, alkenyl, alkenyloxy, alkoxymethyl or alkenyloxymethyl; $Z^4$ denotes a single covalent bond, —COO— or —$CH_2CH_2$—; and $R^9$ is alkyl or alkenyl.

$R^6$, $R^7$, $R^8$ and $R^9$ each preferably have a maximum of 12 carbon atoms, especially a maximum of 7 carbon atoms. Preferred alkenyl groups are 3E-alkenyl, 4-alkenyl or on a cyclohexane ring also 1E-alkenyl. 2E-Alkenyloxy and 3-alkenyloxy are preferred alkenyloxy groups.

The mixtures in accordance with the invention which have a chiral tilted smectic phase can preferably contain, in addition to one or more optically active compounds of formula I, one or more compounds of the following formulas as components of the carrier material:

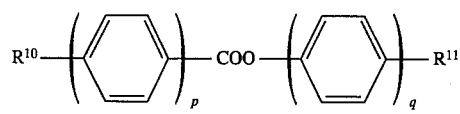

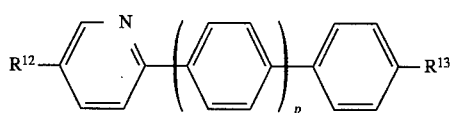

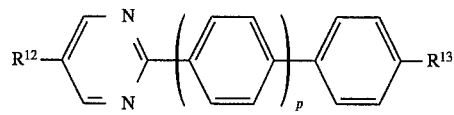

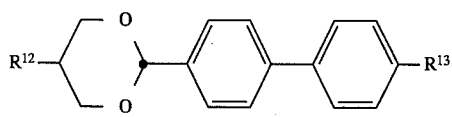

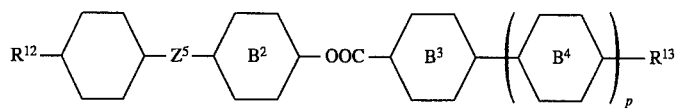

wherein p and q each independently are the integer 0 or 1; $R^{10}$ and $R^{11}$ each independently are alkyl, alkoxy, alkanoyloxy, alkoxycarbonyl, alkenyl or alkenyloxy; $R^{12}$ is alkyl or alkenyl; $R^{13}$ is alkyl, alkoxy, alkenyl or alkenyloxy; rings $B^2$, $B^3$ and $B^4$ each independently are 1,4-phenylene or halogen-substituted 1,4-phenylene; and $Z^5$ is a single covalent bond, —$CH_2CH_2$—, —$CH_2O$—, —COO— or —OOC—.

$R^{10}$, $R^{11}$, $R^{12}$ and $R^{13}$ each preferably have a maximum of 18 carbon atoms, especially about 5–12 carbon atoms. 2-Fluoro-1,4-phenylene and 2,3-difluoro-1,4-phenylene are preferred halogen-substituted 1,4-phenylene groups. Those compounds of formulas XIII–XVII in which $R^{11}$ or $R^{13}$ is alkoxy or alkenyloxy are in general preferred.

The preparation of the liquid crystalline mixtures and of the electro-optical devices can be effected in a manner known per se.

The invention is illustrated in more detail by the following Examples. Optical antipodes of the compounds of formula I have in each case the same phase transition temperatures and induce the same absolute values of the spontaneous polarization and of the twisting, but with opposite signs. The abbreviations used for the characterization of the phase transitions have the following significances C stands for crystalline, S stands for smectic, $S_A$, $S_B$, $S_C$ etc. stand for smectic A, B, C etc., $S_C^*$, $S_F^*$ etc. stand for chiral smectic C, F etc., N stands for nematic, N* stands for cholesteric, I stands for isotropic.

Unless indicated otherwise (e.g., the use of other than past tense verbs), the examples were carried out as written.

EXAMPLE 1

A mixture of 3.0 g of (2S,3R)-2-octyl-1,3-butanediol, 3.07 g of 4'-cyano-4-biphenylcarboxaldehyde, 0.1 ml of 1N sulfuric acid and 30 ml of toluene was placed under nitrogen in a round flask having a magnetic stirrer, water separator and condenser. The mixture was heated to reflux for 3 hours while separating water. The cooled reaction mixture was poured into aqueous sodium hydrogen carbonate solution and treated with methylene chloride. The aqueous phase was separated and extracted twice with methylene chloride. The combined organic phases were washed twice with water, dried over magnesium sulfate, filtered and evaporated. Recrystallization of the crude product obtained (5.84 g) from a mixture of 200 ml of hexane and 25 ml of ethyl acetate gave 4.97 g of 4'-[(2S,4R,5S)-5-octyl-4-methyl-1,3-dioxan-2-yl]-4-cyanobi-phenyl with m.p. (C-$S_A$) 114.5° C., cl.p. ($S_A$-I) 128.4° C.

The (2S,3R)-2-octyl-1,3-butanediol used as the starting material was prepared as follows:

a) A mixture of 83.5 g of diisopropylamine and 400 ml of tetrahydrofuran was treated dropwise at –20° C. within 30 minutes with 500 ml of a 1.6M solution of butyllithium (0.800 mol) in hexane. The mixture was stirred at –20° C. to –50° C. for a further 30 minutes. Subsequently, the mixture was treated dropwise at –50° C. within 30 minutes with a solution of 50 g (0.378 mol) of ethyl (3R)-3-hydroxybutyrate in 250 ml of tetrahydrofuran and stirred at –30° C. for a further 30 minutes. Thereafter, the reaction mixture was treated dropwise at –50° C. within 30 minutes with a solution of 108 g of 1-bromooctane (0.560 mol) in 96.5 g of hexamethylphosphoric acid triamide. The reaction mixture was left to warm to room temperature and was stirred at 25° C. for a further 3 hours. Subsequently, the brown reaction solution was poured into 1.3 l of water and extracted three times with ethyl acetate. The organic phases were washed with saturated sodium chloride solution, dried over sodium sulfate, filtered and concentrated. High vacuum distillation of the brown oil obtained (128 g) gave 54 g of ethyl (2S,3R)-3-hydroxy-2-octylbutyrate with b.p. 99° C./0.03 Torr and $[a]_D$=+6.2° (c=1% in chloroform).

b) A suspension of 33.5 g (0.883 mol) of lithium aluminium hydride in 980 ml of diethyl ether was treated dropwise at room temperature within 30 minutes with a solution of 54 g of ethyl (2S,3R)-3-hydroxy-2-octyl-butyrate in 250 ml of diethyl ether. Subsequently, the reaction mixture was heated to reflux for 2.5 hours and then cooled to 0° C. Thereafter, the reaction mixture was treated dropwise with 100 ml of acetone and then with saturated sodium carbonate solution until a precipitate had formed. The ether phase was decanted off and filtered. The residue in the reaction flask was triturated a further twice with 1 l of diethyl ether each time and in each case the ether phase was decanted off and filtered. The ether phased were combined and concentrated to dryness. There were thus obtained 45 g of crude product as a yellow oil. High vacuum distillation up to an oil bath temperature of 160° C. gave as the residue 40 g of (2S,3R)-2-octyl-1,3-butanediol with $[a]_D$=+18.7° (c=1% in chloroform).

The following compounds can be prepared in an analogous manner:

4'-[(2S,4R,5S)-5-Decyl-4-methyl-1,3-dioxan-2-yl]-4-cyanobiphenyl, m.p. (C-$S_A$) 115,2° C., cl.p. ($S_A$-I) 130.6° C.;

4-[trans-4-[(2S,4R,5S)-5-octyl-4-methyl-1,3-dioxan-2-yl] cyclohexyl]benzonitrile, m.p. (C-N*) 65.3° C., cl.p. (N*-I) 91.2° C.;

4-[trans-4-[(2S,4R,5S)-5-octyl-4-methyl-1,3-dioxan-2-yl] cyclohexyl]-1-fluorobenzene, m.p. 63.5° C.;

4-[trans-4-[(2S,4R,5S)-5-octyl-4-methyl-1,3-dioxan-2-yl] cyclohexyl]-1,2-difluorobenzene, m.p. 32.9° C.;

4-[trans-4-[(2S,4R,5S)-5-octyl-4-methyl-1,3-dioxan-2-yl] cyclohexyl]-1-chlorobenzene, m.p. 66.7° C.;

4-[trans-4-[(2S,4R,5S)-5-octyl-4-methyl-1,3-dioxan-2-yl] cyclohexyl]-1-chloro-2-fluorobenzene, m.p. 40° C.;

4-[trans-4-[(2S,4R,5S)-5-(2-propenyl)-4-methyl-1,3 -dioxan-2-yl]-cyclohexyl]benzonitrile, m.p. 87.2° C.;

5-[(2S,4R,5S)-5-octyl-4-methyl-1,3-dioxan-2-yl]-2-(4 -decyloxyphenyl)pyrimidine, m.p. (C-N*) 67.5° C., cl.p. (N*-I) 106.7° C.;

5-[(2S,4R,5S)-5-decyl-4-methyl-1,3-dioxan-2-yl]-2-(3 -fluoro-4-hexyloxyphenyl)pyridine, m.p. (C-N*) 72.2° C., cl.p. (N*-I) 87,7°.

EXAMPLE 2

8.8 g of terephthalaldehyde were treated with a solution of 25 g of (2S,3)-2-octyl-1,3-butanediol in 500 ml of toluene while gassing with nitrogen in a sulfonation flask having a stirrer, condenser and water separator. Subsequently, the mixture was treated with 1 ml of 1N sulfuric acid and heated to reflux for 18 hours. Thereafter, the reaction mixture was cooled to room temperature, treated with 1.5 ml of trimethylamine and partitioned in 500 ml of diethyl ether and 500 ml of saturated sodium hydrogen carbonate solution. The aqueous phase was separated and extracted twice with 300 ml of diethyl ether each time. The organic phases were washed twice with 400 ml of saturated sodium hydrogen carbonate solution each time and once with 400 ml of water, dried over sodium sulfate, filtered and concentrated. Chromatographic purification of the crude product obtained (31 g) on silica gel with petroleum ether/ethyl acetate (vol. 95:5) and two-fold recrystallization from hexane gave 19.1 g of 1,4-bis-[(2S,4R,5S)-5-octyl-4 -methyl-1,3-dioxan-2-yl]benzene as white crystals with m.p. (C-I) 80,4° C. and $[a]_D$=+32.0° (c=1% in chloroform).

EXAMPLE 3

A mixture of 4.93 g of 4'-[(2S,4R,5S)-5-octyl-4-methyl-1,3 -dioxan-2-yl]-4-biphenylcarboxylic acid, 2.28 ml of (R)-2-octanol, 3.72 g of N,N'-dicyclohexyl-carbodiimide, 205 mg of 4-(dimethylamino)pyridine and 450 ml of methylene chloride was stirred for 4 hours while gassing with nitrogen. Subsequently, the reaction mixture was filtered and the filtrate was evaporated. The crude product obtained (11.28 g) was suspended in 150 ml of methylene chloride. The suspension was filtered and the filtrate was evaporated. Crystallization of the yellow liquid obtained (7.62 g) at −20° C. in hexane, separation of crystalline impurities by filtration, concentration of the filtrate and purification of the residue on basic aluminium oxide with methylene chloride gave 4.40 g of 4'-[(2S,4R,5S)-5-octyl-4 -methyl-1,3-dioxan-2-yl]-4-biphenyl carbonic acid (R)-2-octyl ester, m.p. −25° C. and $[a]_D$=−13.1° (c=0,7% in chloroforme).

The 4'-[(2S,4R,5S)-5-octyl-4-methyl-1,3-dioxan-2-yl]-4-biphenylcarboxylic acid used as the starting material was prepared as follows:

4.97 g of 4'-[(2S,4R,5S)-5-octyl-4-methyl-1,3-dioxan-2-yl)-4-cyanobiphenyl was treated with a solution of 7.1 g of potassium hydroxide in 70 ml of diethylene glycol while gassing with nitrogen. The mixture was heated to 180° C. for 2.5 hours. Thereafter, the reaction mixture was cooled to 70° C., diluted with 150 ml of water and adjusted to pH 9 with 1N hydrochloric acid. The solution was cooled with ice, treated with 250 ml of methylene chloride and adjusted to pH 3–3.5 with 1N hydrochloric acid. The aqueous phase was separated and extracted three times with methylene chloride. The combined organic phases were washed three times with water, dried over magnesium sulfate, filtered and evaporated. This gave 4.93 g of 4'-[(2S,4R,5S)-5-octyl-4-methyl-1,3-dioxan-2-yl]-4-biphenylcarboxylic acid as a yellowish, solid residue.

The following compounds can be prepared in an analogous manner:

4-[(2S,4R,5S)-5-(2-Propenyl)-4-methyl-1,3-dioxan-2-yl]-benzoic acid (R)-2-octyl ester, isotropic oil;

4-[(2S,4R,5S)-5-octyl-4-methyl-1,3-dioxan-2-yl ]-benzoic acid (R)-2-octyl ester, isotropic oil;

4-[(2S,4R,5S)-5-decyl-4-methyl-1,3-dioxan-2-yl]-benzoic acid (R)-2-hexyl ester, isotropic oil;

4-[(2S,4R,5S)-5-decyl-4-methyl-1,3-dioxan-2-yl]-benzoic acid (R)-2-octyl ester, isotropic oil;

4'-[(2S,4R,5S)-5-decyl-4-methyl-1,3-dioxan-2-yl]-4-biphenylcarboxylic acid (R)-2-octyl ester, m.p. (C-I) 21.6° C.;

4'-[(2S,4R,5S)-5-octyl-4-methyl-1,3-dioxan-2-yl]-4-biphenylcarboxylic acid (R)-1-(isobutyloxycarbonyl)ethyl ester, m.p. (C-I) 57.5° C.;

4-[trans-4-[(2S,4R,5S)-5-octyl-4-methyl-1,3-dioxan-2-yl] cyclohexyl]benzoic acid (R)-2-octyl ester, m.p. (C-I) 24.8° C.

EXAMPLE 4

A mixture of 380 mg of 4-[(2S,4R,5S)-5-octyl-4-methyl-1,3-dioxan-2-yl]phenol, 185 mg of (S)-2-fluorocaproic acid, 333 mg of N,N'-dicyclohexylcarbodiimide, 20 mg of 4-(dimethylamino)pyridine and 40 ml methylene chloride was stirred at room temperature under nitrogen for 16.5 hours. Subsequently, the suspension was filtered and the filtrate was evaporated on a rotary evaporator. The crude product (1.0 g) was suspended in 50 ml of methylene chloride, the suspension was filtered and the filtrate was evaporated. Recrystallization of the white, solid residue (0.5 g) from hexane gave 0.4 g of 0.4 g of 1-[(2S,4R,5S)-5-octyl-4-methyl-1,3-dioxan-2-yl]-4-[(S)-2-fluorohexanoyloxy] benzene as white crystals with m.p. (C-I) 58.8° C. and $[a]_D$=+16.7° (c=1% in chloroform).

The 4-[(2S,4R,5S)-5-octyl-4-methyl-1,3-dioxan-2-yl] phenol used as the starting material was prepared as follows:

A mixture of 320 mg of (2S,3R)-2-octyl-1,3-butanediol, 193 mg of p-hydroxybenzaldehyde, 0.1 ml of 1N sulfuric acid and 20 ml of toluene was placed under nitrogen in a round flask having a magnetic stirrer, water separator and condenser. The mixture was heated to reflux for 3 hours while separating water. The cooled reaction mixture was poured into aqueous sodium hydrogen carbonate solution and treated with diethyl ether. The aqueous phase was separated and extracted three times with diethyl ether. The combined organic phases were washed three times with round flask having a magnetic stirrer, water separator and condenser. The mixture was heated to reflux for 3 hours while separating water. The cooled reaction mixture was poured into aqueous sodium hydrogen carbonate solution and treated with diethyl ether. The aqueous phase was separated and extracted three times with diethyl ether. The combined organic phases were washed three times with water, dried over magnesium sulfate, filtered and evaporated. Recrystallization of the yellowish, solid residue (480 mg) from hexane/ethyl acetate (vol. 25:1) gave 410 mg of 4-[(2S,4R,5S)-5-octyl-4-methyl-1,3-dioxan-2-yl]phenol as yellowish crystals with [a]$_D$=+27° (c=1% in chloroform).

The following compounds can be prepared in an analogous manner:

4-Octyloxybenzoic acid 4-[(2S,4R,5S)-5-octyl-4-methyl-1,3-dioxan-2-yl]phenyl ester, m.p. (C-S) 52° C., S-N* 57.4° C., cl.p. (N*-I) 101° C.;

4-hexyloxybenzoic acid 4-[(2S,4R,5S)-5-decyl-4-methyl-1,3-dioxan-2-yl]phenyl ester, m.p. (C-N*) 77° C., cl.p. (N*-I) 101° C.;

4-hexyloxybenzoic acid 4-[(2S,4R,5S)-5-decyl-4-methyl-1,3-dioxan-2-yl]-3-chlorophenyl ester, m.p. (C-I) 47.5° C.

EXAMPLE 5

A solution of 1.7 g of 4'-[(2S,4R,5S)-5-octyl-4-methyl-1,3-dioxan-2-yl]-4-cyanobiphenyl in 12 ml of toluene was treated with 4.6 ml of diisobutylaluminium hydride at 0° C. within 10 minutes while gassing with nitrogen. The reaction mixture was stirred for a further 3 hours without cooling and then treated cautiously with ice/water. The mixture was partitioned in diethyl ether/water, adjusted to pH 6 with 1N sulfuric acid and the layers separated, the aqueous phase was extracted 3 more times with diethyl ether. The organic phases were washed twice with water, dried over magnesium sulfate, filtered and evaporated. The crude 4'-[(2S,4R,5S)-5-octyl-4-methyl-1,3 -dioxan-2-yl]-4-biphenylcarboxaldehyde obtained was transformed to in analogy to example 1 into 4,4'-Bis-[(2S,4R,5S)-5-octyl-4-methyl-1,3-dioxan-2-yl]-biphenyl; m.p. (C-N*) 95.3° C., cl.p. (N*-I) 120.5° C.

EXAMPLE 6

The following liquid crystal basic mixture B M-1 was used to measure the induced pitch and its temperature dependence in liquid crystal materials:

5.36 wt % of 4'-ethyl-4-cyanobiphenyl,
3.18 wt % of 4'-propyl-4-cyanobiphenyl,
6.08 wt % of 4'-butyl-4-cyanobiphenyl,
6.53 wt % of 4-(trans-4-propylcyclohexyl)benzonitrile,
14.67 wt % of 4-(trans-4-pentylcyclohexyl)benzonitrile,
5.21 wt % of 4-ethyl-1-(trans-4-propylcyclohexyl)-benzene,
16.54 wt % of 4-ethoxy-1-[2-(trans-4-propylcyclohexyl)ethyl]benzene,
5.60 wt % of 4"-pentyl-4-cyano-p-terphenyl,
5.71 wt % of 4'-(trans-4-pentylcyclohexyl)-4-cyano-biphenyl,
15.95 wt % of 1-[2-(trans-4-butylcyclohexyl)ethyl]-4-(trans-4-pentylcyclohexyl)benzene,
4.74 wt % of 4-[2-(trans-4-butylcyclohexyl)ethyl]-4'-(trans-4-pentylcyclohexyl)biphenyl,
7.59 wt % of 4-[2-(trans-4-butylcyclohexyl)ethyl]-4'-(trans-4-pentylcyclohexyl)-1,1'-ethylene-dibenzene,
2.84 wt % of trans-4-[2-(trans-4-propylcyclohexyl)ethyl]cyclohexane carboxylic acid 4-cyanophenyl ester;

m.p. <−30° C., cl.p. (N-I) 90° C.; We=8.5, Wn=0.139 and h=22 mPa"s measured at 22° C.

The twisting capacity of the optically active dopant and its temperature dependence is characterized by the parameters A, B and C corresponding to the serial progression:

$$\frac{1}{pc} = A + BT_1 + CT_1^2$$

wherein p, c and $T_1$ have the following significances:

$T_1$=T-22° C.

T=temperature in °C.

p=pitch in mm (a positive value is a clockwise helical structure and a negative value is an anticlockwise helical structure).

c=concentration of the optically active dopant in wt. %.

Basic mixture BM-1 (99 wt. %) was in each case mixed with 1 wt. % of one of the following dopants of formula I:

D-1=4'-[(2S,4R,5S)-5-octyl-4-methyl-1,3 -dioxan-2-yl]-4-biphenylcarboxylic acid (R)-2-octyl ester, D-2=4-[(2S,4R,5S)-5-decyl-4-methyl-1,3 -dioxan-2-yl]-benzoic acid (R)-2-octyl ester, D-3=4-[(2S,4R,5S)-5-octyl-4-methyl-1,3 -dioxan-2-yl]-benzoic acid (R)-2-octyl ester, D-4=4'-[(2S,4R,5S)-5-decyl-4-methyl-1,3 -dioxan-2-yl]-4-cyanobiphenyl, D-5=4'-[(2S,4R,5S)-5-decyl-4-methyl-1,3-dioxan-2-yl]-4-biphenylcarboxylic acid (R)-2-octyl ester, D-6=4,4'-bis-[(2S,4R,5S)-5-octyl-4-methyl-1,3-dioxan-2-yl]biphenyl, D-7=1,4-bis-[(2S,4R,5S)-5-octyl-4-methyl-1,3 -dioxan-2-yl]benzene, D-8=4-[trans-4-[(2S,4R,5S)-5-octyl-4-methyl-1,3-dioxan-2-yl]cyclohexyl]benzonitrile.

The helical pitch p at 22° C., the change $WT_c$ in the clearing point and the values of A, B and C of the cholesteric mixtures obtained are given in Table 1.

TABLE 1

| Dopant | p [μm] | ΔT$_c$ [°C.] | A [$10^{-2} \cdot \mu m^{-1} \cdot$ wt.-%$^1$] | B [$10^{-4} \cdot \mu m^{-1} \cdot$ wt.-%$^{-1} \cdot$ °C.$^{-1}$] | C [$10^{-6} \cdot \mu m^{-1} \cdot$ wt-%$^{-1} \cdot$ °C.$^{-2}$] |
|---|---|---|---|---|---|
| D-1 | 6.79 | −0.9 | 14.72 | 1.757 | −1.138 |
| D-2 | 6.5 | −1.1 | 15.42 | −2.946 | −4.192 |
| D-3 | 6.30 | −4.2 | 15.864 | 0.703 | 0.789 |
| D-4 | 14.9 | −1.5 | 6.699 | 0.832 | 0.444 |
| D-5 | 7.5 | −2.5 | 13.52 | 1.315 | −1.480 |
| D-6 | 12.2 | −0.3 | 8.476 | 2.806 | 1.028 |
| D-7 | 7.4 | −1.8 | 16.26 | 2.729 | −2.461 |
| D-8 | 15.8 | −1.4 | 6.308 | −0.328 | 0.690 |

EXAMPLE 7

The following cholesteric mixtures CM-1 to CM-6 illustrate the use of several chiral dopants for the production of a short helical pitch with low temperature dependence. For this purpose, several nematic basic mixtures were mixed with a combination of 3 or 4 chiral dopants. The cholesteric mixtures obtained are especially suitable for cholesteric filters and are characterized by a low temperature dependence of the wavelength $g_{max}$ of the selectively reflected, circularly polarized light. The values of $g_{max}$ measured at different temperatures T are compiled in Table 2. The abbreviations of the components used in the Mixture Examples have the following significances:

2PP=4'-ethyl-3-cyanobiphenyl,
3PP=4'-propyl-4-cyanobiphenyl,
4PP=4'-butyl-cyanobiphenyl,
3CP=4-(trans-4-propylcyclohexyl)benzonitrile,
5CP=4-(trans-4-pentylcyclohexyl)benzonitrile,
3CP2=4-ethyl-1-(trans-4-propylcyclohexyl)benzene,
3CAPO2=4-ethoxy-1-[2-(trans-4-propylcyclohexyl)ethyl]benzene,
5CAPO2=4-ethoxy-1-[2-(trans-4-pentylcyclohexyl)-ethyl]benzene,
5PPP=4"-pentyl-4-cyano-p-terphenyl,
CPP=4'-(trans-4-pentylcyclohexyl)-4 -cyanobiphenyl,
5CPAC4=1-[2-(trans-4-butylcyclohexyl)ethyl]-4-(trans-4-pentylcyclohexyl)benzene,
5CPPAC4=4-[2-(trans-4-butylcyclohexyl)ethyl]-4-(trans-4-pentylcyclohexyl)biphenyl,
5CPAPAC4=4-[2-(trans-4-butylcyclohexyl)ethyl]-4'-(trans-4-pentylcyclohexyl)-1,1'-ethylenedibenzene,
3CACEP=trans-4-[2-(trans-4-propylcyclohexyl)-ethyl]cyclohexanecarboxylic acid 4 -cyano-phenyl ester,
1d(3)CCO1=trans-4-methoxy-1-[trans-4-(3E-pentenyl)-cyclohexyl]cyclohexane,
1d(1)CC101=trans-4-methoxymethyl-1-[trans4 -(1E-propenyl)cyclohexyl]cyclohexane,
0d(3)CCO2=trans-4-ethoxy-1-[trans-4-(3-butenyl)-cyclohexyl]cyclohexane,
0d(4)CCO2=trans-4-ethoxy-1-[trans-4-(4-pentenyl)-cyclohexyl]cyclohexane,
1d(3)CPO2=4-ethoxy-1-[trans-4-(3E-pentenyl)cyclohexyl]benzene,
3CPOd(3)1=4-(2E-butenyloxy)-1-(trans-4-propylcyclohexyl)benzene,
5CPOd(3)1=4-(2E-butenyloxy)-1-(trans-4-pentyl cyclohexyl)benzene,
1d(3)CPP2=4'-ethyl-4-[trans-4-(3E-pentenyl)cyclohexyl]biphenyl,
1d(3)CPP3=4'-propyl-[trans-4-(3E-pentenyl)cyclohexyl]biphenyl,
3CEPCd(3)1=trans-4-propylcyclohexane carboxylic acid 4-[trans-4-(3E-pentenyl)cyclohexyl]phenylester,
0d(3)CP=4-[trans-4-(3-butenyl)cyclohexyl]benzonitrile,
1d(1)CP=4-[trans-4-(1E-propenyl)cyclohexyl]benzonitrile,
4PP(1)P5=5-(4-butylphenyl)-2-(4-pentylphenyl)pyrimidine,
2CP(1)P5=5-(trans-4-ethylcyclohexyl)-2-(4-pentylphenyl)pyrimidine,
3PPt1=4-(1-propynyl)-4'-propylbiphenyl,
D-7=1,4-bis-[(2S,4R,5S)-5-octyl-4-methyl-1,3-dioxan-2-yl]benzene,
D-2=4-[(2S,4R,5S)-5-decyl-4-methyl-1,3-dioxan-2-yl]benzoic acid (R)-2 -octyl ester,
D-10=(4S,5S)-2-[trans-4-(4-cyanophenyl)cyclohexyl]-1,3-dioxolane-4,5-dicarboxylic acid diethyl ester,
D-11=(S)-4'-(2-methylbutyl)-4-cyanobiphenyl.

Mixture CM-1

4.350 wt. % of 2PP
2.580 wt. % of 3PP
4.930 wt. % of 4PP
5.300 wt. % of 3CP
11.900 wt. % of 5CP
4.230 wt. % of 3CP2
13.420 wt. % of 3CAPO2
4.540 wt. % of 5PPP
4.630 wt. % of 5CPP
12.940 wt. % of 5CPAC4
3.850 wt. % of 5CPPAC4
6.160 wt. % of 5CPAPAC4
2.310 wt. % of 3CACEP
7.700 wt. % of D-7
7.310 wt. % of D-10
3.850 wt. % of D-2

Mixture CM-2

4,220 wt. % of 2PP
2,500 wt. % of 3PP
4,780 wt. % of 4PP
5,140 wt. % of 3CP
11,540 wt. % of 5CP
4,100 wt. % of 3CP2
13,020 wt. % of 3CAPO2
4,410 wt. % of 5PPP
4,490 wt. % of 5CPP
12,550 wt. % of 5CPAC4
3,730 wt. % of 5CPPAC4
5,970 wt. % of 5CPAPAC4
2,240 wt. % of 3CACEP
8,700 wt. % of D-7
8,260 wt. % of D-10
4,350 wt. % of D-2

Mixture CM-3

3.190 wt. % of 1d(3)CCO1
7.960 wt. % of 1d(1)CC101
5.570 wt. % of 0d(3)CCO2
3.180 wt. % of 0d(4)CCO2
2.390 wt. % of 1d(3)CPO2
3.980 wt. % of 3CPOd(3)1
4.780 wt. % of 5CPOd(3)1
4.780 wt. % of 3CAPO2
4.780 wt. % of 5CAPO2
3.980 wt. % of 1d(3)CPP2
5.570 wt. % of 1d(3)CPP3
6.370 wt. % of CPAC4
3.980 wt. % of CEPCd(3)1
3.980 wt. % of 0d(3)CP
3.180 wt. % of 1d(1
2.390 wt. % of 4PP(1)P5
2.390 wt. % of 2CP(1)P5
2.390 wt. % of 5CPPAC4
4.780 wt. % of 3PPt1
6.710 wt. % of D-7
6.320 wt. % of D-10
4.190 wt. % of D-2
3.160 wt. % of D-11

Mixture CM-4

3.070 wt. % of 1d(3)CO1
7.680 wt. % of 1d(1)CC101
5.380 wt. % of 0d(3)CCO2
3.070 wt. % of 0d(4)CCO2
2.300 wt. % of 1d(3)CPO2
3.840 wt. % of 3CPOd(3)1
4.610 wt. % of 5CPOd(3)1
4.610 wt. % of 3CAPO2
4.610 wt. % of 5CAPO2
3.840 wt. % of 1d(3)CPP2
5.370 wt. % of 1d(3)CPP3
6.140 wt. % of 5CPAC4
3.840 wt. % of 3CEPCd(3)1
3.840 wt. % of 0d(3)CP

-continued 3.070 wt. % of 1d(1)CP
2.300 wt. % of 4PP(1)P5
2.300 wt. % of 2CP(1)P5
2.300 wt. % of 5CPPAC4
4.610 wt. % of 3PPt1
7.650 wt. % of D-7
7.200 wt. % of D-10
4.770 wt. % of D-2
3.600 wt. % of D-11

Mixture CM-5

2.970 wt. % of 1d(3)CCO1
7.420 wt. % of 1d(1)CC101
5.190 wt. % of 0d(3)CCO2
2.970 wt. % of 0d(4)CCO2
2.230 wt. % of 1d(3)CPO2
3.710 wt. % of 3CPOd(3)1
4.450 wt. % of 5CPOd(3)1
4.450 wt. % of 3CAPO2
4.450 wt. % of 5CAPO2
3.710 wt. % of 1d(3)CPP2
5.190 wt. % of 1d(3)CPP3
5.930 wt. % of 5CPAC4
3.710 wt. % of 3CEPCd(3)1
3.710 wt. % of 0d(3)CP
2.970 wt. % of 1d(1)CP
2.230 wt. % of 4PP(1)P5
2.230 wt. % of 2CP(1)P5
2.230 wt. % of 5CPPAC4
4.450 wt. % of 3PPt1
8.500 wt. % of D-7
8.000 wt. % of D-10
5.300 wt. % of D-2
4.000 wt. % of D-11

Mixture CM-6

4.050 wt. % of 2PP
2.400 wt. % of 3PP
4.590 wt. % of 4PP
4.930 wt. % of 3CP
11.080 wt. % of 5CP
3.930 wt. % of 3CP2
12.490 wt. % of 3CAPO2
4.230 wt. % of 5PPP
4.310 wt. % of 5CPP
12.040 wt. % of 5CPAC4
3.580 wt. % of 5CPPAC4
5.730 wt. % of 5CPAPAC4
2.140 wt. % of 3CACEP
10.000 wt. % of D-7
9.500 wt. % of D-10
5.000 wt. % of D-2

TABLE 2

| T [°C.] | $\lambda_{max}$ [nm] | | | | | |
|---|---|---|---|---|---|---|
| | CM-1 | CM-2 | CM-3 | CM-4 | CM-5 | CM-6 |
| 0 | 610 | 527 | 616 | 540 | 467 | 456 |
| 10 | 610 | 527 | 614 | 540 | 467 | 460 |
| 20 | 610 | 534 | 613 | 540 | | |
| 22 | | | | | 471 | 464 |
| 30 | 618 | 535 | 612 | 541 | 471 | 470 |
| 40 | 621 | 540 | 611 | 540 | 476 | 473 |
| 50 | 636 | 548 | 624 | 544 | 478 | 477 |

EXAMPLE 8

The chiral tilted smectic mixtures SM-1 to SM-3 set forth in Table 3 illustrate the use of the chiral dopants of formula I in a tilted smectic liquid crystal. 1/(pc) characterizes the twisting capacity of the chiral dopant, with p and c having the significances given in Example 5. $P_s$ denotes the spontaneous polarization (extrapolated to 100 wt. %). The concentrations given in Table 3 are in wt. %. The abbreviations used for the components have the following significances:

10OPEPAC5=4-Decyloxybenzoic acid 4-[2-(trans-4-pentyl-cyclohexyl)ethyl]phenyl ester,
11OPEPAC5=4-undecyloxybenzoic acid 4-[2-(trans-4-pentylcyclohexyl)ethyl]phenyl ester,
12OPEPAC5=4-dodecyloxybenzoic acid 4-[2-(trans-4-pentylcyclohexyl)ethyl]phenyl ester,
7P(1)PO8=2-(4-octyloxyphenyl)-5-heptyl-pyrimidine,
9P(1)PO6=2-(4-hexyloxyphenyl)-5-nonyl-pyrimidine,
9P(1)PO9=2-(4-nonyloxyphenyl)-5-nonyl-pyrimidine,
10P(1)PO10=2-(4-decyloxyphenyl)-5-decyl-pyrimidine,
D-12=4-octyloxybenzoic acid 4-[(2S,4R,5S)-5-octyl-4-methyl-1,3-dioxan-2 -yl]phenyl ester,
D-13=4-hexyloxybenzoic acid 4-[(2S,4R,5S)-5-decyl-4-methyl-1,3-dioxan-2 -yl]phenyl ester,
D-14=4-hexyloxybenzoic acid 4-[(2S,4R,5S)-5-decyl-4-methyl-1,3 -dioxan-2-yl]- 3-chlorophenyl ester.

TABLE 3

| | SM-1 | SM-2 | SM-3 |
|---|---|---|---|
| 10OPEPAC5 | 23.4% | 23.2% | 23.4% |
| 11OPEPAC5 | 11.7% | 11.6% | 11.7% |
| 12OPEPAC5 | 11.7% | 11.6% | 11.7% |
| 7P(1)PO8 | 4.3% | 4.3% | 4.3% |
| 9P(1)PO6 | 14.6% | 14.6% | 14.7% |
| 9P(1)PO9 | 14.6% | 14.6% | 14.7% |
| 10P(1)PO10 | 12.7% | 12.6% | 12.8% |
| D-12 | 7.0% | — | — |
| D-13 | — | 7.5% | — |
| D-14 | — | — | 6.5% |
| 1/(pc) [mm$^{-1}$ "wt. %$^{-1}$"]. | +12 | +4.5 | +8.3 |
| $P_s$ [nC/cm$^2$] | −67 | −33 | +24 |
| Transition temperature [°C.] | 59.9($S_C$*-N*) 98.8 (N*-I) | 58($S_C$*-SA) | 51($S_C$*-SA) |

We claim:

1. An optically active compound of the formula:

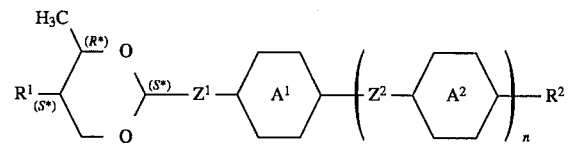

wherein n is the integer 0 or 1; $Z^1$ is a single covalent bond or —CH$_2$CH$_2$—; $Z^2$ is a single covalent bond, —CH$_2$CH$_2$—, —CH$_2$O—, —OCH$_2$—, —COO— or —OOC—; rings $A^1$ and $A^2$ each independently are trans-1,4-cyclohexylene, 1,4-phenylene, 1,4-phenylene substituted with at least one substituent selected from the group consisting of halogen, cyano, or methyl, pyridin-2,5-diyl, or pyrimidine-2,5-diyl; $R^2$ is a group $R^4$ or a group of the formula

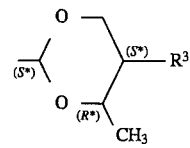

$R^4$ is cyano, halogen, —OCY$^1$F$_2$, —CY$^1$F$_2$ or an alkyl, alkenyl, alkoxy, alkenyloxy, alkoxyalkyl, alkenyloxyalkyl, alkoxycarbonyl, alkoxycarbonylalkoxy, alkoxycarbonylalkoxycarbonyl or alkanoyloxy group having 1 to 18 carbon atoms, any of which may be unsubstituted or substituted with at least one substituent selected from the group consisting of halogen, cyano or methyl; $Y^1$ is hydrogen or fluorine; $R^1$ and $R^3$ each are an alkyl, alkoxy, alkenyl, alkenyloxy, alkoxyalkyl or alkenyloxyalkyl group having 1 to 18 carbon atoms, which are unsubstituted or substituted with at least one fluorine; and (S*) and (R*) denote the relative configurations of the chiral carbon atoms, and optical antipodes thereof.

2. The compound according to claim 1, wherein ring $A^2$ is 1,4-phenylene or halogen-substituted 1,4-phenylene, $Z^2$ is a single covalent bond, —CH$_2$CH$_2$— or —OOC—, and $Z^1$ is a single covalent bond.

3. The compound according to claim 1, wherein ring $A^1$ is pyridine-2,5-diyl, pyrimidine-2,5-diyl, trans-1,4-cyclohexylene or 1,4-phenylene, which is unsubstituted or substituted with at least one of halogen, cyano or methyl.

4. The compound according to claim 1, selected from the group consisting of compounds of the formulas

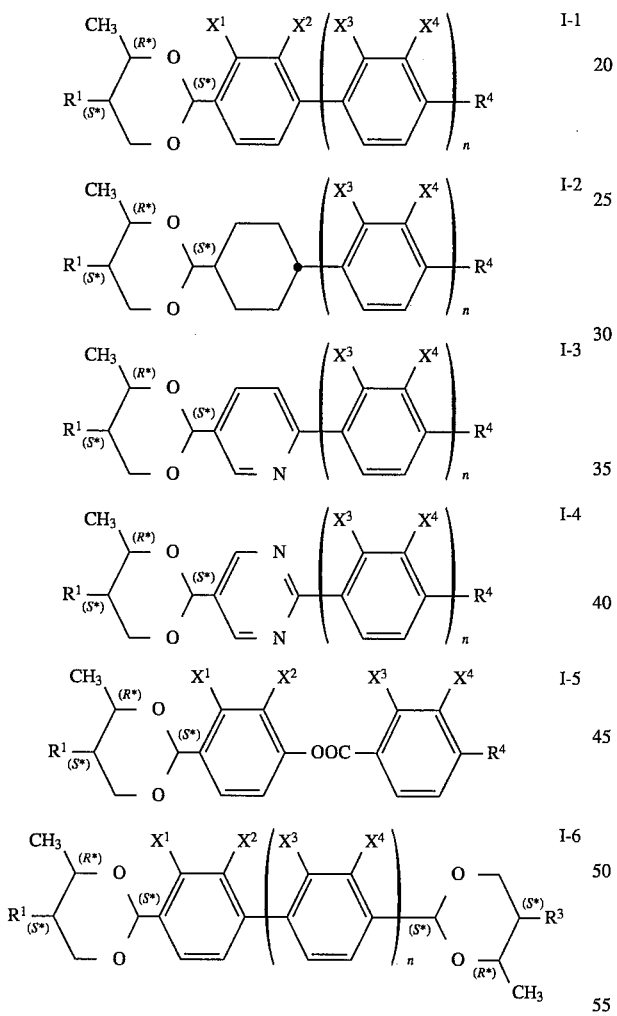

wherein $R^4$ is cyano, halogen, —OCY$^1$F$_2$, —CY$^1$F$_2$, or alkyl, alkenyl, alkoxy, alkenyloxy, alkoxyalkyl, alkenyloxyalkyl, alkoxycarbonyl, alkoxycarbonylalkoxy, alkoxycarbonylalkoxycarbonyl or alkanoyloxy, any of which latter ten moieties may be unsubstituted or substituted with at least one of halogen, cyano or methyl; $X^1$, $X^2$, $X^3$ and $X^4$ each independently are hydrogen or halogen; and $Y^1$, n, $R^1$, $R^3$, (S*) and (R*) have the above significances.

5. The compound according to claim 4, wherein $X^1$, $X^2$, $X^3$ and $X^4$ each independently are hydrogen, fluorine or chlorine.

6. The compound according to claim 5, wherein $X^1$ is hydrogen, fluorine or chlorine, $X^2$ and $X^3$ each are hydrogen, and $X^4$ is hydrogen, fluorine or chlorine.

7. The compound according to claim 1, wherein $R^1$ and $R^3$ each are alkyl.

8. The compounds according to claim 1, wherein $R^4$ is cyano, fluorine, chlorine, difluoromethoxy, trifluoromethoxy, difluoromethyl, trifluoromethyl, alkyl, alkoxy, alkoxycarbonyl, 1-(alkoxycarbonyl)ethoxycarbonyl, alkanoyloxy, 2-fluoroalkanoyloxy, alkenyl or alkenyloxy.

9. The compounds according to claim 1, wherein $R^1$, $R^3$ and $R^4$ each independently have a total of 1–18 carbon atoms.

10. The compound according to claim 9, wherein $R^1$, $R^3$ and $R^4$ each independently have a total of 1–12 carbon atoms.

11. A liquid crystalline mixture having at least two components, wherein at least one component is an optically active compound of the formula:

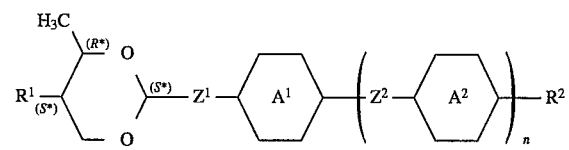

wherein n is the integer 0 or 1; $Z^1$ is a single covalent bond or —CH$_2$CH$_2$—; $Z^2$ is a single covalent bond, —CH$_2$CH$_2$—, —CH$_2$O—, OCH$_2$—, —COO— or —OOC—; rings $A^1$ and $A^2$ each independently are trans-1,4-cyclohexylene, 1,4-phenylene, 1,4-phenylene substituted with at least one substituent selected from the group consisting of halogen, cyano, or methyl, pyridin-2,5-diyl, or pyrimidine- 2,5-diyl; $R^2$ is a group $R^4$ or a group of the formula

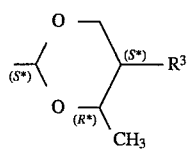

$R^4$ is cyano, halogen, —OCY$^1$F$_2$, —CY$^1$F$_2$ or an alkyl, alkenyl, alkoxy, alkenyloxy, alkoxyalkyl, alkenyloxyalkyl, alkoxycarbonyl, alkoxycarbonylalkoxy, alkoxycarbonylalkoxycarbonyl or alkanoyloxy group having 1 to 18 carbon atoms, any of which may be unsubstituted or substituted with at least one substituent selected from the group consisting of halogen, cyano or methyl; $Y^1$ is hydrogen or fluorine; $R^1$ and $R^3$ each are an alkyl, alkoxy, alkenyl, alkenyloxy, alkoxyalkyl or alkenyloxyalkyl group having 1 to 18 carbon atoms, which are unsubstituted or substituted with at least one fluorine; and (S*) and (R*) denote the relative configurations of the chiral carbon atoms, and optical antipodes thereof.

12. The liquid crystalline mixture according to claim 11, which includes at least one optically active compound of formula I and a liquid crystalline carrier material having a nematic, cholesteric or tilted smectic phase.

13. The liquid crystalline mixture according to claim 11, wherein the total amount of compound of formula I is about 0.1 to about 40 wt. % of the mixture.

14. An electro-optical cell comprising:

(A) two plate means;

(b) liquid crystal means disposed between two plate means and including a compound of the formula:

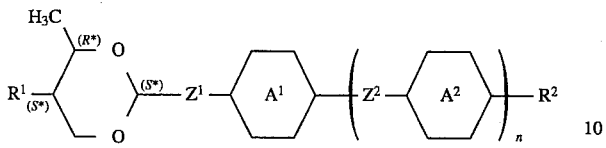

wherein n is the integer 0 or 1; $Z^1$ is a single covalent bond or —CH$_2$CH$_2$—; $Z^2$ is a single covalent bond, —CH$_2$CH$_2$—, —CH$_2$O—, OCH$_2$—, —COO— or —OOC—; rings $A^1$ and $A^2$ each independently are trans-1,4-cyclohexylene, 1,4-phenylene, 1,4-phenylene substituted with at least one substituent selected from the group consisting of halogen, cyano, or methyl, pyridin-2,5-diyl, or pyrimidine- 2,5-diyl; $R^2$ is a group $R^4$ or a group of the formula

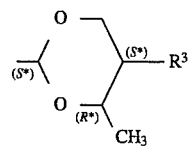

$R^4$ is cyano, halogen, —OCY$^1$F$_2$, —CY$^1$F$_2$ or an alkyl, alkenyl, alkoxy, alkenyloxy, alkoxyalkyl, alkenyloxyalkyl, alkoxycarbonyl, alkoxycarbonylalkoxy, alkoxycarbonylalkoxycarbonyl or alkanoyloxy group having 1 to 18 carbon atoms, any of which may be unsubstituted or substituted with at least one substituent selected from the group consisting of halogen, cyano or methyl; $Y^1$ is hydrogen or fluorine; $R^1$ and $R^3$ each are an alkyl, alkoxy, alkenyl, alkenyloxy, alkoxyalkyl or alkenyloxyalkyl group having 1 to 18 carbon atoms, which are unsubstituted or substituted with at least one fluorine; and (S*) and (R*) denote the relative configurations of the chiral carbon atoms, and optical antipodes thereof; and (c) means for applying an electric potential to said plate means.

* * * * *